United States Patent [19]

Jenko et al.

[11] Patent Number: 4,467,093
[45] Date of Patent: Aug. 21, 1984

[54] PROCESS FOR PREPARING A 1,4-DIHYDROPYRIDINE DERIVATIVE

[75] Inventors: Branko Jenko, Ljubljana-Polje; Igor Langof, Ljubljana, both of Yugoslavia

[73] Assignee: LEK, Tovarna Farmacevtskih in Kemicnih Izdelkov, N.Sol.O., Ljubljana, Yugoslavia

[21] Appl. No.: 402,487

[22] Filed: Jul. 27, 1982

[30] Foreign Application Priority Data

Aug. 19, 1981 [YU] Yugoslavia ............................ 2005/81

[51] Int. Cl.$^3$ ............................................ C07D 213/55
[52] U.S. Cl. ..................................... 546/321; 546/319
[58] Field of Search ................................ 546/319, 321

[56] References Cited

U.S. PATENT DOCUMENTS 3,485,847 12/1969 Bossert et al. ....................... 546/321
3,644,627  2/1972 Bossert et al. ....................... 424/266
4,297,519 10/1981 Ertel ..................................... 568/424

OTHER PUBLICATIONS

Barton et al., Comprehensive Organic Chemistry, vol. I, pp. 1108–1110, Pergamon Press, (1979).
Hendrickson et al., Organic Chemistry, Third Edition, pp. 90–98, 453–456, and 963, McGraw Hill-Kogakusha Ltd. Pub., (1970).
Bossert et al., Chemical Abstracts, vol. 70, No. 21, 96, 641d, May 26, 1969.

McOmie, Protective Groups in Organic Chemistry, pp. 327–331, Plenum Publishing Corp., 1973.
The Merck Index, Ninth Edition, p. ONR-40, Merck & Co., Inc., pub. 1976.

Primary Examiner—Alan L. Rotman
Attorney, Agent, or Firm—Pollock, Vande Sande & Priddy

[57] ABSTRACT

In the process for preparing 4-(2'-nitrophenyl-2,6-dimethyl)-3,5-dicarbmethoxy-1,4-dihydropyridine of the formula

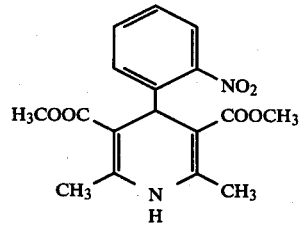

2-nitrobenzaldehyd-diacetate, methyl acetoacetate and ammonia are reacted in the presence of an inert organic solvent, such as methanol, and in the presence or absence of an organic base, such as pyridine, at a temperature of between 20° and 150° C. The compound is a valuable medicine for the treatment of angina pectoris.

8 Claims, No Drawings

PROCESS FOR PREPARING A 1,4-DIHYDROPYRIDINE DERIVATIVE

The present invention relates to a new process for preparing 4-(2'-nitrophenyl)-2,6-dimethyl-3,5-dicarbmethoxy-1,4-dihydropyridine of the formula

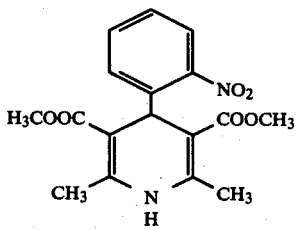

I which is known also by its generic name Nifedifin and which is, due to its coronary-vasodilatory activity, a valuable medicine for the treatment of angina pectoris. 4-(2'-nitrophenyl)-2,6-dimethyl-3,5-dicarbmethoxy-1,4-dihydropyridine is a known compound and was described for the first time in German Pat. No. 1 670 827. According to the method described in said German patent, the compound can be obtained by reacting 2-nitrobenzaldehyde, methyl acetoacetate and ammonia in an inert organic solvent, e.g. methanol. The method is based on Hantzsch's synthesis of pyridines as said ester of 1,4-dihydropyridine-3,5-dicarboxylic acid is a stable intermediate, synthesized according to this method. It is known to prepare the starting compound for this synthesis, i.e. 2-nitrobenzaldehyde, by oxidation of 2-nitrotoluene with chromic acid in the presence of sulphuric acid and acetic anhyride (Houben-Weyl, Methoden der organischen Chemie, Band VII, Teil I, Sauerstoffverbindungen II., 1954, 143). The intermediate compound, 2-nitrobenzaldehyde-diacetate of the formula

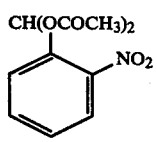

which is formed in the reaction, is a stable compound which can be further hydrolyzed to give 2-nitrobenzaldehyde. The yield of this synthesis is about 60% of the theory.

According to the process of the invention, a reagent, i.e. 2-nitrobenzaldehyde-diacetate of the formula II, is used for the first time in the synthesis of 4-(2'-nitrophenyl)-2,6-dimethyl-3,5-dicarbmethoxy-1,4-dihydropyridine. Thus the expensive starting material 2-nitrobenzaldehyde was subtituted by the less expensive 2-nitrobenzaldehyde-diacetate, which can be prepared as described hereinbefore. The compound is reacted with methyl acetoacetate and ammonia in the presence of an inert organic solvent, such as methanol, and in the presence or absence of an organic base, such as pyridine, at the temperature of between 20° and 150° C. This process wherein one synthesis step can be omitted—since there is no need for the preliminary hydrolysis of 2-nitrobenzaldehyde-diacetate of the formula II to the corresponding 2-nitrobenzaldehyde—represents a new and simplified Hantzsch's method for the synthesis of pyridines.

The invention is illustrated but not limited by the following Examples.

EXAMPLE 1

2-Nitrobenzaldehyde-diacetate (0.1 mole, 25.4 g), methyl acetoacetate (0.2 mole, 23.2 g) and NH4OH (12 ml) were heated in methanol (20 ml) in the presence of pyridine for several (7) hours. After cooling to 15° C. the precipitated product was filtered off. The crude product was crystallized from acetic acid to yield 4-(2'-nitrophenyl)-2-6-dimethyl-3-5-dicarbmethoxy-1,4-dihydropyridine (21.7 g, 62% of the theory), m.p. 172°–174° C.

EXAMPLE 2

2-Nitrobenzaldehyde-diacetate (0.1 mole, 25.4 g), methyl acetoacetate (0.21 mole, 26 g), NH4OH (12 ml) and methanol (45 ml) were heated under reflux for 5 hours. After cooling to 15° C. the precipitated product was filtered off. The crystallization of the crude product from acetic acid yielded 4-(2'-nitrophenyl)-2,6 di-methyl-3,5-dicarbmethoxy-1,4-dihydropyridine (19.0 g, 55% of the theory), m.p. 173°–174° C.

What is claimed is:

1. A process for preparing 4-(2'-nitrophenyl-2,6-dimethyl)-3,5-dicarbomethoxy-1,4-dihydropyridine of the formula

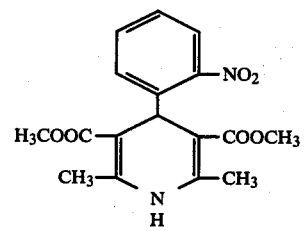

I which comprises reacting 2-nitrobenzaldehyde diacetate, methyl acetoacetate, and ammonia in the presence of an inert organic solvent at a temperature of between 20° C. and 150° C.

2. The process of claim 1 wherein said solvent is methanol.

3. The process of claim 2 wherein the 2-nitrobenzaldehyde diacetate is reacted in the absence of an organic base.

4. The process of claim 2 wherein the 2-nitrobenzaldehyde diacetate is reacted in the presence of an organic base.

5. The process of claim 4 wherein said organic base is pyridine.

6. The process of claim 1 wherein the 2-nitrobenzaldehyde diacetate is reacted in the absence of an organic base.

7. The process of claim 1 wherein the 2-nitrobenzaldehyde diacetate is reacted in the presence of an organic base.

8. The process of claim 7 wherein said organic base is pyridine.

* * * * *